US010010499B2

(12) United States Patent
Chiang et al.

(10) Patent No.: US 10,010,499 B2
(45) Date of Patent: Jul. 3, 2018

(54) METHODS OF USING MICRONEEDLE VACCINE FORMULATIONS TO ELICIT IN ANIMALS PROTECTIVE IMMUNITY AGAINST RABIES VIRUS

(71) Applicants: MERIAL, INC., Duluth, GA (US); Georgia Tech Research Corporation, Atlanta, GA (US)

(72) Inventors: Yu-Wei Chiang, Athens, GA (US); Mark R. Prausnitz, Atlanta, GA (US); Kristopher Daniel DeWitt, Bogart, GA (US); Jaya Arya, Atlanta, GA (US)

(73) Assignees: MERIAL INC., Duluth, GA (US); Georgia Tech Research Corporation, Atlanta, GA (US)

( * ) Notice: Subject to any disclaimer, the term of this patent is extended or adjusted under 35 U.S.C. 154(b) by 0 days.

(21) Appl. No.: 14/930,831

(22) Filed: Nov. 3, 2015

(65) Prior Publication Data
US 2016/0120799 A1    May 5, 2016

Related U.S. Application Data

(60) Provisional application No. 62/074,436, filed on Nov. 3, 2014.

(51) Int. Cl.
C12N 7/00        (2006.01)
A61K 9/00        (2006.01)
A61K 39/205      (2006.01)
A61K 39/12       (2006.01)
A61M 37/00       (2006.01)
A61K 39/00       (2006.01)
A61B 5/15        (2006.01)
A61B 17/20       (2006.01)

(52) U.S. Cl.
CPC ............ *A61K 9/0021* (2013.01); *A61K 39/12* (2013.01); *A61K 39/205* (2013.01); *C12N 7/00* (2013.01); *A61B 5/150984* (2013.01); *A61B 17/20* (2013.01); *A61B 17/205* (2013.01); *A61K 2039/5254* (2013.01); *A61K 2039/5256* (2013.01); *A61K 2039/53* (2013.01); *A61K 2039/54* (2013.01); *A61K 2039/545* (2013.01); *A61K 2039/552* (2013.01); *A61M 37/0015* (2013.01); *A61M 2037/0046* (2013.01); *A61M 2037/0061* (2013.01); *C12N 2760/20034* (2013.01); *C12N 2760/20134* (2013.01)

(58) Field of Classification Search
None
See application file for complete search history.

(56) References Cited

U.S. PATENT DOCUMENTS

| 5,547,467 A | 8/1996 | Pliquett et al. |
| 5,667,491 A | 9/1997 | Pliquett et al. |
| 5,911,223 A | 6/1999 | Weaver et al. |
| 6,334,856 B1 | 1/2002 | Allen et al. |
| 6,503,231 B1 | 1/2003 | Prausnitz et al. |
| 6,611,707 B1 | 8/2003 | Prausnitz et al. |
| 6,743,211 B1 | 6/2004 | Prausnitz et al. |
| 7,273,458 B2 | 9/2007 | Prausnitz et al. |
| 7,344,499 B1 | 3/2008 | Prausnitz et al. |
| 7,918,814 B2 | 4/2011 | Prausnitz et al. |
| 8,197,435 B2 | 6/2012 | Prausnitz et al. |
| 8,257,324 B2 | 9/2012 | Prausnitz et al. |
| 8,506,530 B2 | 8/2013 | Laermer et al. |
| 8,636,713 B2 | 1/2014 | Prausnitz et al. |
| 9,114,238 B2 * | 8/2015 | Singh ............... A61K 9/0021 |
| 9,216,213 B2 * | 12/2015 | Maki ............... A61K 39/205 |
| 2004/0071675 A1 * | 4/2004 | Mazarakis ............ A61K 48/00 424/93.21 |
| 2009/0182306 A1 | 7/2009 | Lee et al. |
| 2009/0318846 A1 | 12/2009 | Prausnitz et al. |
| 2010/0312191 A1 | 12/2010 | Allen et al. |
| 2012/0269846 A1 | 10/2012 | Maki et al. |
| 2013/0209511 A1 | 8/2013 | Mebatsion et al. |
| 2013/0338632 A1 | 12/2013 | Kaplan et al. |

FOREIGN PATENT DOCUMENTS

WO    WO 2012/023044 A1    2/2012

OTHER PUBLICATIONS

Lodmell et al. One-time intradermal DNA vaccination in ear pinnae one year prior to infection protects dogs against rabies virus. Vaccine. Jan. 23, 2006;24(4):412-6.*
J Arya et al. "Dissolving Microneedle Patch for Rabies DNA Vaccination in Dogs." AAPS, Nov. 2, 2014 (Nov. 2, 2014). XP055242367.
Ray N B et al. "Nanogram quantities of plasmid DNA encoding the rabies virus glycoprotein protect mice against lethal rabies virus infection." Vaccine. Elsevier Ltd. GB. vol. 15. No. 8. Jun. 1, 1997 (Jun. 1, 1997). pages 892-895. XP004075678.
Peter C Demuth et al, "Vaccine delivery with microneedle skin patches in nonhuman primates." Nature Biotechnology. vol. 31. No. 12. Dec. 6, 2013, pp. 1082-1085. XP055242577.
Sushma Kommareddy et al, "Dissolvable microneedle patches for the delivery of cell-culture-derived influenza vaccine antigens." Journal of Pharmaceutical Sciences. vol. 101. No. 3. Mar. 20, 2012, pp. 1021-1027. XP055227032.
Yeu-Chun Kim et al, Microneedles for drug and vaccine delivery. Advanced Drug Delivery Reviews. vol. 64. No. 14. May 1, 2012, pp. 1547-1568. XP055242608.

(Continued)

Primary Examiner — Michelle S Horning
(74) Attorney, Agent, or Firm — Judy Jarecki-Black; Ruoying Chen; Merial Inc.

(57) ABSTRACT

The present invention relates to microneedle vaccine formulations, as well as methods of use thereof to provide animals, including canines, protective immunity against infection and disease caused by rabies viruses. Once placed onto the skin of the animals, the microneedle formulations dissolve quickly into the surrounding skin, where the antigens then elicit in the animals high and protective levels of rabies virus neutralizing antibodies.

28 Claims, 3 Drawing Sheets

(56) References Cited

OTHER PUBLICATIONS

Philippe E. Laurent et al, "Safety and efficacy of novel dermal and epidermal microneedle delivery systems for rabies vaccination in healthy adults" Vaccine. vol. 28. No. 36. Jun. 30, 2010, pp. 5850-5856. XP055242571.
Hyemee Suh et al. Microneedle patches for vaccine delivery. Clinical and Experimental Vaccine Research. vol. 3. No. 1. Jan. 1, 2014, p. 42. XP055242377.

* cited by examiner

SEQUENCE LISTING

<160> NUMBER OF SEQ ID NOS: 2

<210> SEQ ID NO 1
<211> LENGTH: 524
<212> TYPE: PRT
<213> ORGANISM: Rabies virus

<400> SEQUENCE: 1

```
Met Val Pro Gln Ala Leu Leu Phe Val Pro Leu Leu Val Phe Pro Leu
1               5                   10                  15

Cys Phe Gly Lys Phe Pro Ile Tyr Thr Ile Pro Asp Lys Leu Gly Pro
            20                  25                  30

Trp Ser Pro Ile Asp Ile His His Leu Ser Cys Pro Asn Asn Leu Val
        35                  40                  45

Val Glu Asp Glu Gly Cys Thr Asn Leu Ser Gly Phe Ser Tyr Met Glu
    50                  55                  60

Leu Lys Val Gly Tyr Ile Leu Ala Ile Lys Met Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
            100                 105                 110

Cys Arg Ala Ala Tyr Asn Trp Lys Met Ala Gly Asp Pro Arg Tyr Glu
        115                 120                 125

Glu Ser Leu His Asn Pro Tyr Pro Asp Tyr Arg Trp Leu Arg Thr Val
    130                 135                 140

Lys Thr Thr Lys Glu Ser Leu Val Ile Ile Ser Pro Ser Val Ala Asp
145                 150                 155                 160

Leu Asp Pro Tyr Asp Arg Ser Leu His Ser Arg Val Phe Pro Ser Gly
                165                 170                 175

Lys Cys Ser Gly Val Ala Val Ser Ser Thr Tyr Cys Ser Thr Asn His
            180                 185                 190

Asp Tyr Thr Ile Trp Met Pro Glu Asn Pro Arg Leu Gly Met Ser Cys
        195                 200                 205

Asp Ile Phe Thr Asn Ser Arg Gly Lys Arg Ala Ser Lys Gly Ser Glu
    210                 215                 220

Thr Cys Gly Phe Val Asp Glu Arg Gly Leu Tyr Lys Ser Leu Lys Gly
225                 230                 235                 240

Ala Cys Lys Leu Lys Leu Cys Gly Val Leu Gly Leu Arg Leu Met Asp
                245                 250                 255

Gly Thr Trp Val Ala Met Gln Thr Ser Asn Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Arg Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
            340                 345                 350

Thr Trp Asn Glu Ile Leu Pro Ser Lys Gly Cys Leu Arg Val Gly Gly
        355                 360                 365
```

```
Arg Cys His Pro His Val Asn Gly Val Phe Phe Asn Gly Ile Ile Leu
    370                 375                 380

Gly Pro Asp Gly Asn Val Leu Ile Pro Glu Met Gln Ser Ser Leu Leu
385                 390                 395                 400

Gln Gln His Met Glu Leu Leu Glu Ser Ser Val Ile Pro Leu Val His
                405                 410                 415

Pro Leu Ala Asp Pro Ser Thr Val Phe Lys Asp Gly Asp Glu Ala Glu
            420                 425                 430

Asp Phe Val Glu Val His Leu Pro Asp Val His Asn Gln Val Ser Gly
        435                 440                 445

Val Asp Leu Gly Leu Pro Asn Trp Gly Lys Tyr Val Leu Leu Ser Ala
450                 455                 460

Gly Ala Leu Thr Ala Leu Met Leu Ile Ile Phe Leu Met Thr Cys Cys
465                 470                 475                 480

Arg Arg Val Asn Arg Ser Glu Pro Thr Gln His Asn Leu Arg Gly Thr
                485                 490                 495

Gly Arg Glu Val Ser Val Thr Pro Gln Ser Gly Lys Ile Ile Ser Ser
            500                 505                 510

Trp Glu Ser His Lys Ser Gly Gly Glu Thr Arg Leu
        515                 520

<210> SEQ ID NO 2
<211> LENGTH: 1572
<212> TYPE: DNA
<213> ORGANISM: Rabies virus

<400> SEQUENCE: 2
atggttcctc aagctctcct gtttgtaccc cttctggttt ttccgttgtg ttttggaaaa      60
ttccctattt acacaatccc agacaagctt ggtccctgga gccgattga catacatcac     120 ctcagctgcc caaacaattt ggtagtggag gacgaaggat gcaccaacct gtcagggttc    180
tcctacatgg aacttaaagt tggatacatc ttagccataa aaatgaacgg ttcacttgc     240 acaggcgttg tgacggaggc tgaaacctac actaacttcg ttggttatgt cacaaccacg    300
ttcaaaagaa agcatttccg cccaacacca gatgcatgta gagccgcgta caactggaag    360
atggccggtg accccagata tgaagagtct ctacacaatc cgtaccctga ctaccgctgg    420
cttcgaactg taaaaaccac caaggagtct ctcgttatca tatctccaag tgtagcagat    480
ttggacccat atgacagatc ccttcactcg agggtcttcc ctagcgggaa gtgctcagga    540
gtagcggtgt cttctaccta ctgctccact aaccacgatt acaccatttg gatgcccgag    600
aatccgagac tagggatgtc ttgtgacatt tttaccaata gtagagggaa gagagcatcc    660
aaagggagtg agacttgcgg cttttgtagat gaaagaggcc tatataagtc tttaaaagga    720
gcatgcaaac tcaagttatg tggagttcta ggacttagac ttatggatgg aacatgggtc    780
gcgatgcaaa catcaaatga aaccaaatgg tgccctcccg atcagttggt gaacctgcac    840
gactttcgct cagacgaaat tgagcacctt gttgtagagg agttggtcag aagagagag    900 gagtgtctgg atgcactaga gtccatcatg acaaccaagt cagtgagttt cagacgtctc    960
agtcatttaa gaaacttgtg ccctgggttt ggaaaagcat ataccatatt caacaagacc   1020
ttgatggaag ccgatgctca ctacaagtca gtcagaactt ggaatgagat cctcccttca   1080
aaagggtgtt taagagttgg ggagggtgt catcctcatg tgaacggggt gttttcaat   1140 ggtataaatt taggacctga cggcaatgtc ttaatccag agatgcaatc atcctcctc     1200 cagcaacata tggagttgtt ggaatcctcg gttatccccc ttgtgcaccc cctggcagac   1260
```

-continued

```
ccgtctaccg ttttcaagga cggtgacgag gctgaggatt ttgttgaagt tcaccttccc    1320
gatgtgcaca atcaggtctc aggagttgac ttgggtctcc cgaactgggg gaagtatgta    1380
ttactgagtg caggggccct gactgccttg atgttgataa ttttcctgat gacatgttgt    1440
agaagagtca atcgatcaga acctacgcaa cacaatctca gagggacagg gagggaggtg    1500
tcagtcactc cccaaagcgg gaagatcata tcttcatggg aatcacacaa gagtgggggt    1560
gagaccagac tg                                                        1572
```

METHODS OF USING MICRONEEDLE VACCINE FORMULATIONS TO ELICIT IN ANIMALS PROTECTIVE IMMUNITY AGAINST RABIES VIRUS

CROSS-REFERENCE TO RELATED APPLICATIONS

This application claims the benefit of priority to U.S. Provisional Application No. 62/074,436 filed Nov. 3, 2014, which is incorporated herein by reference in its entirety.

INCORPORATION BY REFERENCE

All of the references cited herein are incorporated by reference herein in their entirety.

FIELD OF THE INVENTION

The present invention relates to microneedle vaccine formulations, and particularly to methods of use thereof to provide animals with protective immunity against rabies.

BACKGROUND

Rabies is a disease that can occur in all warm-blooded species and is caused by rabies virus. Infection with rabies virus followed by the outbreak of the clinical features in nearly all instances results in death of the infected species. In Europe, the USA and Canada wild life rabies still exists and is an important factor in the cause of most human rabies cases that occur. On the other hand, urban rabies constitutes the major cause of human rabies in developing countries. In fact, more than three billion people in Asia and Africa are at high risk of contracting rabies and fifty thousand die of the disease each year. Virtually all of these human cases occur in developing countries as the result of exposure to rabid dogs. For this reason, there is an urgent need for more effective rabies vaccination of community dogs in these countries.

Rabies virus is a non-segmented negative-stranded RNA virus of the Rhabdoviridae family. Rabies virus virions are composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleocapsid (N) protein in combination with two minor proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane. The G protein, also referred to as spike protein, is responsible for cell attachment and membrane fusion in rabies virus and additionally is the main target for the host immune system. The amino acid region at position 330 to 340 (referred to as antigenic site III) of the G protein has been identified to be responsible for the virulence of the virus, in particular the Arg residue at position 333. All rabies virus strains have this virulence determining antigenic site III in common. Existing vaccines typically comprise various forms of the Rabies G protein (e.g. subunit, nucleic acids encoding the G protein, inactivated, recombinant, and the like).

One drawback of many existing vaccines is storage stability. One possible solution to this problem is to produce a "microneedle patch," which incorporates an effective rabies antigen. A microneedle patch (FIG. 1) contains an array of micron-scale, solid needles, which encapsulate vaccine in a water-soluble matrix (see e.g. U.S. Pat. No. 7,918,814, U.S. Pat. No. 8,257,324, U.S. Pat. No. 8,636,713 and US 2008/0213461, each to Prausnitz & the Georgia Tech Research Corporation, and incorporated into this disclosure, by reference, in their entirety). Within seconds of being applied, the microneedles puncture the skin, can separate from the patch, and can become embedded within the skin where they can dissolve. In the process, the microneedles can deliver the encapsulated vaccine without producing sharps waste.

An ideal rabies vaccine should 1) be safe, inexpensive and easy to formulate, 2) reduce the amount of antigen dose required to achieve effective protection, and 3) be stable at ambient temperature for deployment to the developing countries. However, until this disclosure, it was not known whether Rabies vaccine could be formulated into safe, effective and stable microneedle formulations. Moreover, it was not predictable whether such a microneedle formulation could be used to elicit a safe and protective immune response against subsequent virulent rabies virus challenge.

SUMMARY OF THE INVENTION

The invention is based, in part, on the unexpected and surprising result that nucleic acid-based rabies vaccines can be successfully formulated into bio-absorbable/bio-erodible polymeric microneedles. These formulations have a high level of stability and are effective in eliciting protective immune responses, at significantly lower levels of antigen, compared with conventional parenteral administration.

The invention further encompasses methods, including prime-boost methods, of using the microneedles vaccine compositions to elicit in animals a protective immune response against subsequent challenge with virulent rabies virus, either delivered experimentally, or encountered by the animal naturally.

In an embodiment, the nucleic acid may comprise a modified live vaccinia virus. In another embodiment, the rabies surface glycoprotein gene may be rabies glycoprotein G, which is derived from an ERA strain in one embodiment.

In another embodiment, the vaccinia virus or the vaccinia virus vector may be a Copenhagen strain or a derivative thereof. In another embodiment, the vaccinia virus or the vaccinia virus vector may have a tk– phenotype. In an advantageous embodiment, the vaccinia virus or the vaccinia virus vector may be a Copenhagen strain (or a derivative thereof) and has a tk– phenotype.

In another embodiment, the modified live vaccinia virus may be RABORAL V-RG®.

The invention also provides for a kit for performing any of the above described methods comprising the any of the above described compositions and optionally, instructions for performing the method.

Accordingly, the invention provides a stable, safe and easy to administer microneedle vaccine composition, which is suitable for use in a variety of animals including dogs, cats and pigs.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION OF THE INVENTION

Figure 1:
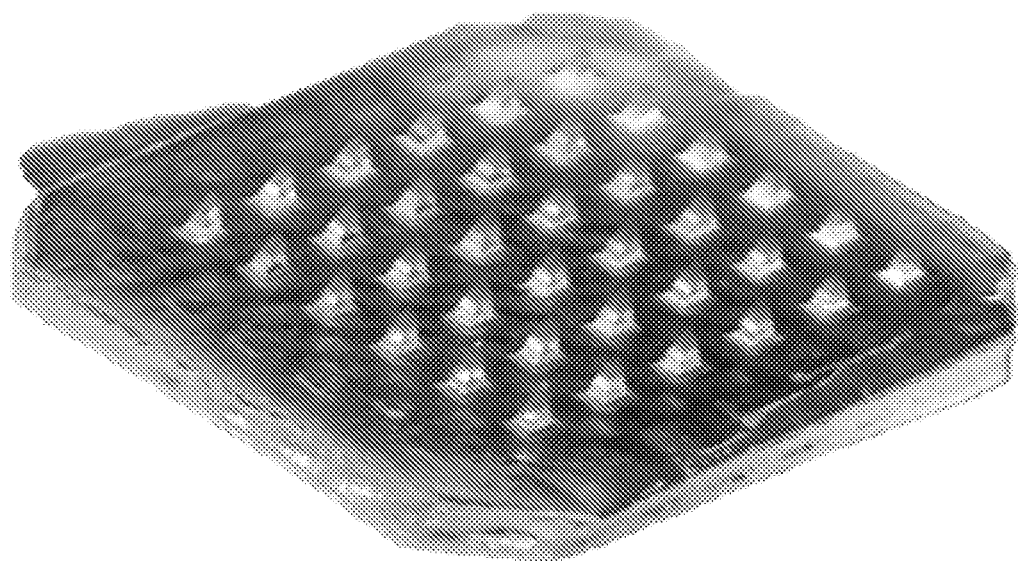
FIG. 1 shows a microneedle patch.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

For convenience, certain terms employed in the Specification, Examples, and appended Claims are collected here.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is also noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

As used herein, the term "animal" includes all vertebrate animals including humans. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (i.e., different isolates of Rabies virus serotypes), from a different species (i.e., isolates from both *Pasteurella haemolytica* and *Pasteurella multocida*), or a vaccine containing a combination of antigens from different genera (for example, a vaccine comprising antigens from *Pasteurella multocida, Salmonella, Escherichia coli, Haemophilus somnus* and *Clostridium*).

As used herein, the term "adjuvant" means a substance added to a vaccine to increase a vaccine's immunogenicity, as compared with its efficacy in absence of the adjuvant. The mechanism of how adjuvants operate is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant, and adjuvants disclosed in U.S. Pat. No. 7,371,395 to Merial Limited, which are herein incorporated by reference in their entirety), *Corynebacterium parvum*,

*Bacillus Calmette Guerin*, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N, N-dioctadecyl-N',N'-bis(2-hydroxyethyl)-propanediamine), paraffin oil, muramyl dipeptide and the like.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The term "purified" as used herein does not require absolute purity; rather, it is intended as a relative term. Thus, for example, a purified immunogen preparation, such as protein or inactivated virus, is one in which the immunogen is more enriched than the immunogen is in its natural environment. An immunogen preparation is herein broadly referred to as "purified" such that the immunogen represents at least 60%, at least 70%, at least 80%, at least 90%, at least 95%, or at least 98%, of the total immunogen content of the preparation. A "crude preparation", which represents the lowest degree of purification, may contain as little as less than 60%, less than 20%, less than 10%, less than 5%, or less than 1% of immunogenic components.

The term "highly purified" as used herein is intended to suggest a "higher degree of purity" as compared to the term "moderately purified". This "higher degree of purity" can include, but is in no way limited to, reduced percentages of contaminants, in an immunological preparation that has been "highly purified" versus an immunological preparation that has been "moderately purified". As discussed herein, "highly purified" immunological preparations will have the lowest to undetectable percentages of contaminants that can cause: reduced desired immune response, increased undesired immune response (e.g. hypersensitivity reaction), or reduced formulation stability. Similarly, an immunological preparation that has been "moderately purified" contains relatively reduced percentages of contaminants versus an immunological preparation that has been "minimally purified", which likewise, has reduced percentages of contaminants versus a preparation designated a "crude preparation".

Contaminants in an immunological preparation can include, but are in no way limited to, substances that contribute negatively to an immunological composition according to the present invention. One of several examples of a contaminant contributing negatively would be a contaminant that reduces the ability of an immunological composition of the present invention to elicit an immune response in animals.

Varying levels of purity (e.g. "highly purified", "moderately purified", and the like) can be achieved using various methods. For example, a combination of chromatography and size exclusion gel filtration can result in a "highly purified" or "moderately purified" immunological preparations. Differences in source/type of immunogens, as well as slight variations in purification procedures can significantly affect the final degree of immunogen purity. In general, as used herein, immunological preparations having the lowest to highest percentage of contaminants will be described as 1) "highly purified, 2) "moderately purified", 3) "minimally purified", 4) "crude preparation", respectively. A "highly purified" preparation will have the lowest level across all types of contaminants. A "moderately purified" preparation will have relatively low levels of most types of contaminants, but may have one type of contaminant in higher abundance than would be observed for a comparable "highly purified" preparation. Likewise, a "minimally purified preparation" will have relatively low levels of some types of contaminants, but may have more than one type of contaminant in higher abundance than a comparable "moderately purified" preparation. As expected, a "crude preparation" has the highest level of contaminants, across all contaminant types, as compared to the other types of preparations discussed herein.

In another embodiment, the rabies glycoprotein is any rabies glycoprotein with a known protein sequence, such as rabies virus glycoprotein G. such as the protein sequences in or derived from the nucleotide sequences in Marissen et al., J Virol. April 2005; 79(8):4672-8; Dietzschold et al., Vaccine. Dec. 9, 2004; 23(4):518-24; Mansfield et al., J Gen Virol. November 2004; 85(Pt 11):3279-83; Sato et al., J Vet Med Sci. July 2004; 66(7):747-53; Takayama-Ito et al., J Neurovirol. April 2004; 10(2):131-5; Li et al., Zhongguo Yi Xue Ke Xue Yuan Xue Bao. December 2003; 25(6):650-4; Hemachudha et al., J Infect Dis. Oct. 1, 2003; 188(7):960-6; Kankanamge et al., Microbiol Immunol. 2003; 47(7):507-19; Maillard et al., Virus Res. June 2003; 93(2):151-8; Irie et al. Microbiol Immunol. 2002; 46(7):449-61; Langevin et al., J Biol Chem. Oct. 4, 2002; 277(40):37655-62; Maillard and Gaudin, J Gen Virol. June 2002; 83(Pt 6):1465-76; Holmes et al., Virology. Jan. 20, 2002; 292(2):247-57; Mebatsion, J Virol. December 2001; 75(23):11496-502; Zhang et al., Zhonghua Shi Yan He Lin Chuang Bing Du Xue Za Zhi. September 2000; 14(3):281-4; Ray et al., Clin Exp Immunol. July 2001; 125(1):94-101; Morimoto et al., Vaccine. May 14, 2001; 19(25-26):3543-51; Morimoto et al., J Neurovirol. October 2000; 6(5):373-81; Bourhy et al., J Gen Virol. October 1999; 80 (Pt 10):2545-57; Kissi et al., J Gen Virol. August 1999; 80 (Pt 8):2041-50; Nakahara et al., Microbiol Immunol. 1999; 43(3):259-70; Matthews et al., J Gen Virol. February 1999; 80 (Pt 2):345-53; Tuffereau et al., EMBO J. Dec. 15, 1998; 17(24):7250-9; Jallet et al. J Virol. January 1999; 73(1):225-33; Wloch et al., Hum Gene Ther. Jul. 1, 1998; 9(10):1439-47; Mellquist et al., Biochemistry. May 12, 1998; 37(19):6833-7; Morimoto et al., Proc Natl Acad Sci USA. Mar. 17, 1998; 95(6):3152-6; Coll, Arch Virol. 1997; 142(10):2089-97; Bracci et al., Blood. Nov. 1, 1997; 90(9):3623-8; Gaudin et al., J Virol. November 1996; 70(11):7371-8; Morimoto et al., Proc Natl Acad Sci USA. May 28, 1996; 93(11):5653-8; Mebatsion et al., Cell. Mar. 22, 1996; 84(6):941-51; Shakin-Eshleman et al., J Biol Chem. Mar. 15, 1996; 271(11):6363-6; Nadin-Davis et al., J Virol Methods. March 1996; 57(1):1-14. Erratum in: J Virol Methods Apr. 26, 1996; 58(1-2):209; Wojczyk et al., Protein Exp. Purif. March 1996; 7(2):183-93; Suzuki et al., J Gen Virol. December 1995; 76 (Pt 12):3021-9; Raux et al., Virology. Jul. 10, 1995; 210(2):400-8; Kasturi et al., J Biol Chem. Jun. 16, 1995; 270(24):14756-61; Otvos et al., Biochim Biophys Acta. May 29, 1995; 1267(1):55-64; Mebatsion et al., J Virol. March 1995; 69(3):1444-51; Wojczyk B, Shakin-Eshleman S H, Doms R W, Xiang Z Q, Ertl H C, Wunner W H, Spitalnik, Biochemistry. Feb. 28, 1995; 34(8):2599-609; Ravkov et al., Virology. Jan. 10, 1995; 206(1):718-23; Ni et al., Microbiol Immunol. 1995; 39(9):693-702; Coll, Arch Virol. 1995; 140(5):827-51; Grabko et al., Dokl Akad Nauk. July 1994; 337(1):117-21; Sakamoto et al., Virus Genes. January 1994; 8(1):35-46; Fodor et al., Arch Virol. 1994; 135(3-4):451-9; Ito et al., Microbiol Immunol. 1994; 38(6):479-82; Shakin-Eshleman et al., Biochemistry. Sep. 14, 1993; 32(36):9465-72; Morimoto et al., Virology. August 1993; 195(2):541-9; van der Heijden et al., J Gen Virol. August 1993; 74 (Pt 8):1539-45; Nishihara et al., Gene. Jul. 30, 1993; 129(2):207-14; Rustici et al., Biopolymers. June 1993; 33(6):961-9; McColl et al., Aust Vet J. March 1993; 70(3):84-9; Bai et al., Virus Res. February 1993; 27(2):101-12; Nishihara et al., Nippon Rinsho. February 1993; 51(2):323-8; Bracci et al., FEBS Lett. Oct. 19, 1992; 311(2):115-8; Tuchiya et al., Virus Res. Sep. 1, 1992; 25(1-2):1-13; Shakin-Eshleman et al., J Biol Chem. May 25, 1992; 267(15):10690-8; Whitt et al., Virology. December 1991; 185(2):681-8; Benmansour et al., J Virol. August 1991; 65(8):4198-203; Burger et al., J Gen Virol. February 1991; 72 (Pt 2):359-67; Dietzschold et al., J Virol. August 1990; 64(8):3804-9; Becker, Virus Genes. February 1990; 3(3):277-84; Prehaud et al., Virology. December 1989; 173(2):390-9 and Wang et al., Chin Med J (Engl). November 1989; 102(11):885-9, the disclosures of which are incorporated by reference in their entireties, may be used in the present invention.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to a rabies glycoprotein polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of a rabies glycoprotein polypeptides and functionally equivalent fragments thereof which may enhance, decrease or not significantly affect properties of the polypeptides encoded thereby. These functionally equivalent variants, derivatives, and fragments display the ability to retain rabies glycoprotein activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

For the purposes of the present invention, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from the "blast.wustl.edu" ftp site. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as (Nref−Ndif)*100/Nref, wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Nref=8; Ndif=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being-considered equal to uracil (U) in RNA sequences.

And, without undue experimentation, the skilled artisan can consult with many other programs or references for determining percent homology.

The invention further encompasses a rabies glycoprotein contained in a vector molecule or an expression vector and operably linked to an enhancer and/or a promoter element if necessary. In an advantageous embodiment, the promoter is a cytomegalovirus (CMV) promoter. In another embodiment, the enhancers and/or promoters include various cell or tissue specific promoters, various viral promoters and enhancers and various rabies glycoprotein DNA sequences isogenically specific for each animal species.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

Elements for the expression of rabies glycoprotein are advantageously present in an inventive vector. In minimum manner, this comprises, consists essentially of, or consists of an initiation codon (ATG), a stop codon and a promoter, and optionally also a polyadenylation sequence for certain vectors such as plasmid and certain viral vectors, e.g., viral vectors other than poxviruses. When the polynucleotide encodes a polyprotein fragment, e.g. rabies glycoprotein, advantageously, in the vector, an ATG is placed at 5' of the reading frame and a stop codon is placed at 3'. Other elements for controlling expression may be present, such as enhancer sequences, stabilizing sequences and signal sequences permitting the secretion of the protein.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491; WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid. The herein cited and incorporated herein by reference documents, in addition to providing examples of vectors useful in the practice of the invention, can also provide sources for non-rabies glycoprotein proteins or fragments thereof, e.g., non-rabies glycoprotein proteins or fragments thereof, cytokines, etc. to be expressed by vector or vectors in, or included in, the compositions of the invention.

The present invention also relates to preparations comprising vectors, such as expression vectors, e.g., therapeutic compositions. The preparations can comprise, consist essentially of, or consist of one or more vectors, e.g., expression vectors, such as in vivo expression vectors, comprising, consisting essentially or consisting of (and advantageously expressing) one or more of a rabies glycoprotein polynucleotides and, advantageously, the vector contains and expresses a polynucleotide that includes, consists essentially of, or consists of a coding region encoding rabies glycoprotein, in a pharmaceutically or veterinarily acceptable carrier, excipient or vehicle. Thus, according to an embodiment of the invention, the other vector or vectors in the preparation comprises, consists essentially of or consists of a polynucleotide that encodes, and under appropriate circumstances the vector expresses one or more other proteins of rabies glycoprotein or a fragment thereof.

According to another embodiment, the vector or vectors in the preparation comprise, or consist essentially of, or consist of polynucleotide(s) encoding one or more proteins or fragment(s) thereof of rabies glycoprotein, the vector or vectors have express of the polynucleotide(s). The inventive preparation advantageously comprises, consists essentially of, or consists of, at least two vectors comprising, consisting essentially of, or consisting of, and advantageously also expressing, advantageously in vivo under appropriate conditions or suitable conditions or in a suitable host cell, polynucleotides from different rabies glycoprotein isolates encoding the same proteins and/or for different proteins, but advantageously for the same proteins. As to preparations containing one or more vectors containing, consisting essentially of or consisting of polynucleotides encoding, and advantageously expressing, advantageously in vivo, rabies glycoprotein, or an epitope thereof, it is advantageous that the expression products be from two, three or more different rabies glycoprotein isolates, advantageously strains. The invention is also directed at mixtures of vectors that contain, consist essentially of, or consist of coding for, and express different rabies proteins.

In an embodiment, the vector is a viral vector, which may be a vaccinia virus vector containing the rabies glycoprotein gene. The rabies glycoprotein may be rabies glycoprotein G derived from the ERA strain. In an advantageous embodiment, the vaccinia virus can be a Copenhagen strain and/or a tk− phenotype. In a particularly advantageous embodiment, the vector is a vaccinia virus vector (Copenhagen strain and tk− phenotype) with the rabies virus glycoprotein G encoded therein, advantageously RABORAL V-RG®.

In one particular embodiment the viral vector is a poxvirus, e.g. a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807), swinepox, raccoonpox, camelpox, or myxomatosis virus.

According to another embodiment of the invention, the poxvirus vector is a canarypox virus or a fowlpox virus vector, advantageously an attenuated canarypox virus or fowlpox virus. In this regard, is made to the canarypox available from the ATCC under access number VR-111. Attenuated canarypox viruses are described in U.S. Pat. No. 5,756,103 (ALVAC) and WO01/05934. Numerous fowlpox virus vaccination strains are also available, e.g. the DIFTOSEC CT strain marketed by MERIAL and the NOBILIS VARIOLE vaccine marketed by INTERVET; and, reference is also made to U.S. Pat. No. 5,766,599 which pertains to the attenuated fowlpox strain TROVAC.

For information on the method to generate recombinants thereof and how to administer recombinants thereof, the skilled artisan can refer documents cited herein and to WO90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and U.S. Pat. No. 5,766,599 inter alia; as to canarypox mention is made of U.S. Pat. No. 5,756,103 inter alia; as to swinepox mention is made of U.S. Pat. No. 5,382,425 inter alia; and, as to raccoonpox, mention is made of WO00/03030 inter alia.

When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters.

Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter 13 L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

Advantageously, for the vaccination of mammals the expression vector is a canarypox or a fowlpox. In this way, there can be expression of the heterologous proteins with limited or no productive replication.

According to one embodiment of the invention, the expression vector is a viral vector, in particular an in vivo expression vector. In an advantageous embodiment, the expression vector is an adenovirus vector, such as a human adenovirus (HAV) or a canine adenovirus (CAV). Advantageously, the adenovirus is a human Ad5 vector, an E1-deleted and/or disrupted adenovirus, an E3-deleted and/or disrupted adenovirus or an E1- and E3-deleted and/or disrupted adenovirus. Optionally, E4 may be deleted and/or disrupted from any of the adenoviruses described above. For example, the human Ad5 vectors expressing a rabies glycoprotein gene described in Yarosh et al. and Lutze-Wallace et al. can be used in methods of the invention (see, e.g., Yarosh et al., Vaccine. September 1996; 14(13):1257-64 and Lutze-Wallace et al., Biologicals. December 1995; 23(4):271-7).

In one embodiment the viral vector is a human adenovirus, in particular a serotype 5 adenovirus, rendered incompetent for replication by a deletion in the E1 region of the viral genome. The deleted adenovirus is propagated in E1-expressing 293 cells or PER cells, in particular PER.C6 (F. Falloux et al Human Gene Therapy 1998, 9, 1909-1917). The human adenovirus can be deleted in the E3 region eventually in combination with a deletion in the E1 region (see, e.g. J. Shriver et al. Nature, 2002, 415, 331-335, F. Graham et al Methods in Molecular Biology Vol 7: Gene Transfer and Expression Protocols Edited by E. Murray, The Human Press Inc, 1991, p 109-128; Y. Ilan et al Proc. Natl. Acad. Sci. 1997, 94, 2587-2592; S. Tripathy et al Proc. Natl. Acad. Sci. 1994, 91, 11557-11561; B. Tapnell Adv. Drug Deliv. Rev. 1993, 12, 185-199; X. Danthinne et al Gene Thrapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter). The CMV-IE promoter is advantageously of murine or human origin. The promoter of the elongation factor 1α can also be used. In one particular embodiment a promoter regulated by hypoxia, e.g. the promoter HRE described in K. Boast et al Human Gene Therapy 1999, 13, 2197-2208), can be used. A muscle specific promoter can also be used (X. Li et al Nat. Biotechnol. 1999, 17, 241-245). Strong promoters are also discussed herein in relation to plasmid vectors. A poly(A) sequence and terminator sequence can be inserted downstream the polynucleotide to be expressed, e.g. a bovine growth hormone gene or a rabbit β-globin gene polyadenylation signal.

In another embodiment the viral vector is a canine adenovirus, in particular a CAV-2 (see, e.g. L. Fischer et al. Vaccine, 2002, 20, 3485-3497; U.S. Pat. Nos. 5,529,780; 5,688,920; PCT Application No. WO95/14102). For CAV, the insertion sites can be in the E3 region and/or in the region located between the E4 region and the right ITR region (see U.S. Pat. Nos. 6,090,393; 6,156,567). In one embodiment the insert is under the control of a promoter, such as a cytomegalovirus immediate-early gene promoter (CMV-IE promoter) or a promoter already described for a human adenovirus vector. A poly(A) sequence and terminator sequence can be inserted downstream the polynucleotide to be expressed, e.g. a bovine growth hormone gene or a rabbit β-globin gene polyadenylation signal.

In another particular embodiment the viral vector is a herpesvirus such as a canine herpesvirus (CHV) or a feline herpesvirus (FHV). For CHV, the insertion sites may be in particular in the thymidine kinase gene, in the ORF3, or in the UL43 ORF (see U.S. Pat. No. 6,159,477). In one embodiment the polynucleotide to be expressed is inserted under the control of a promoter functional in eukaryotic cells, advantageously a CMV-IE promoter (murine or human). In one particular embodiment a promoter regulated by hypoxia, e.g. the promoter HRE described in K. Boast et al Human Gene Therapy 1999, 13, 2197-2208), can be used. A poly(A) sequence and terminator sequence can be inserted downstream the polynucleotide to be expressed, e.g. bovine growth hormone or a rabbit β-globin gene polyadenylation signal.

According to one embodiment of the invention, the expression vector is a plasmid vector or a DNA plasmid vector, in particular an in vivo expression vector. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence.

The term "plasmid" covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form (e.g. digested by a restriction enzyme that only cuts the DNA plasmid a single time), are intended to be within the scope of the invention. The skilled person understands that "plasmid" does not refer to viral vectors.

Each plasmid comprises or contains or consists essentially of, in addition to the polynucleotide encoding a rabies glycoprotein variant, analog or fragment, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO87/03905. The CMV-IE promoter is advantageously a human CMV-IE (Boshart M. et al., Cell., 1985, 41, 521-530) or murine CMV-IE.

In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277).

Functional sub fragments of these promoters, i.e., portions of these promoters that maintain an adequate promoting activity, are included within the present invention, e.g. truncated CMV-IE promoters according to PCT Application No. WO98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156,567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments.

Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO89/01036), the intron II of the rabbit β-globin gene (van Ooyen et al., Science, 1979, 206, 337-344).

As to the polyadenylation signal (polyA) for the plasmids and viral vectors other than poxviruses, use can more be made of the poly(A) signal of the bovine growth hormone (bGH) gene (see U.S. Pat. No. 5,122,458), or the poly(A) signal of the rabbit β-globin gene or the poly(A) signal of the SV40 virus.

According to another embodiment of the invention, the expression vectors are expression vectors used for the in vitro expression of proteins in an appropriate cell system. The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods.

It is understood to one of skill in the art that conditions for culturing a host cell varies according to the particular gene and that routine experimentation is necessary at times to determine the optimal conditions for culturing rabies glycoprotein depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

In an advantageous embodiment, the invention provides for the administration of a therapeutically effective amount of a formulation for the delivery and expression of rabies glycoprotein in a target cell. Determination of the therapeutically effective amount is routine experimentation for one of ordinary skill in the art. In one embodiment, the formulation comprises an expression vector comprising a polynucleotide that expresses rabies glycoprotein and a pharmaceutically or veterinarily acceptable carrier, vehicle or excipient. In an advantageous embodiment, the pharmaceutically or veterinarily acceptable carrier, vehicle or excipient facilitates transfection and/or improves preservation of the vector or protein.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

One skilled in the art can determine the effective plasmid dose to be used for each immunization or vaccination protocol and species from this disclosure and the knowledge in the art.

In an advantageous embodiment, the pharmaceutical and/or therapeutic compositions and/or formulations according to the invention are administered transdermally via a microneedle patch.

In an embodiment, the invention is a safe and effective microneedle rabies virus vaccine composition, which elicits in an animal host a safe and protective immune response against subsequent virulent rabies virus challenge, comprising a plasmid DNA vector expressing a protective rabies antigen, an attenuated recombinant viral vector expressing a protective rabies antigen, or protective rabies virus peptides. The composition may be administered by placing the microneedle patch on the animal's skin, thereby piercing the animal's skin with the microneedles, and releasing the vaccine.

The microneedle rabies vaccine composition may comprise or consist of a vector, which is either an orthopox or avipox virus. The vector may be a vaccinia, canarypox, or fowlpox virus. The microneedle rabies vaccine composition may also comprise a vector that expresses in vivo in the animal host a rabies G protein having the amino acid sequence as set forth n SEQ ID NO:1.

The microneedle rabies vaccine composition may comprise or consist of a plasmid DNA, which expresses the rabies G protein.

The plasmid may be present in an amount between about 5 µg and 50 µg, and may contain a nucleotide sequence encoding the rabies G protein as set forth in SEQ ID NO:1.

The microneedle rabies vaccine composition may provide, sufficient immunostimulation to protect from subsequent challenge greater than 80% of the animals receiving a single dose, and greater than 95% of the animals receiving a second, booster dose.

The microneedle rabies vaccine composition of this disclosure may be used to perform a dose-sparing method. In such a method, the composition contain less than about one-half the dose normally required for a comparable single-needle vaccination.

Accordingly, a dose-sparing microneedle composition may be safely and effectively administered to an animal, to elicit a protective immune response against subsequent exposure to virulent rabies virus. The dose-sparing composition contains less than one-half of the amount of antigen required to elicit a protective immune response using a conventional single needle administration. In one embodiment, less than about one-fifth the amount of antigen is present in the dose-sparing composition, relative to the amount of antigens required in a conventional single needle vaccine composition.

In an embodiment of the dose-sparing method, the vector comprises a modified live vaccinia virus. In another embodiment, the vector expresses the rabies glycoprotein G. In a particular embodiment, the rabies glycoprotein G is derived from an ERA strain. In a very particular embodiment, the vaccinia virus is a Copenhagen strain, and has a tk– phenotype.

In a particular embodiment of the method, the modified live vaccinia virus is RABORAL V-RG®.

In another aspect, the invention provides a method of eliciting in an animal a protective immune response against rabies comprising administering to said animal a therapeutically effective amount of a microneedle composition comprising polymers and a recombinant virus containing a rabies G polynucleotide.

In an embodiment, a first dose is followed by a second booster dose, of the same microneedle composition as the first dose, administered to the animal about twenty-eight days after the first dose.

In another aspect, the invention provides a method of eliciting in an animal a protective immune response against rabies comprising administering to said animal a therapeutically effective amount of a microneedle composition comprising a polymer and a recombinant virus containing a rabies G polynucleotide.

In an embodiment, the rabies G polynucleotide has the sequence as set forth in SEQ ID NO:2.

In an embodiment, the animal is a canidae, a felidae, *homo sapiens*, or a suidae. In another embodiment, the animal is a dog, a bitch, a puppy, a cat or a kitten. The animal may also be a sow, a pig or a piglet.

In an embodiment of the method, the animal is given a second booster dose at about twenty-eight days after the first dose. The immunological response may be protective in greater than 90% of the animals against subsequent challenge with virulent rabies virus, either experimentally delivered, or naturally encountered in the environment.

In an embodiment of the method, the animal may be protected against rabies for at least about one year after administration of the composition.

In another embodiment, the dose may be administered by hand-pressure application of a microneedle patch, and in a range of about 10 µg to about 50 µg per dose. In another embodiment, the dose may be about 30 µg to about 50 µg. In a particular embodiment, the dose may be about 50 µg. In one embodiment, the protection may last at least about 3 years.

In an embodiment, the method is a prime-boost method for vaccinating an animal against rabies, comprising administering to said animal, on two separate occasions, a microneedle vaccine composition comprising: (a) a nucleic acid molecule encoding a rabies G protein; and (b) bio-erodible polymers.

In an embodiment, the two administrations provide protection against rabies for at least one year following the second administration of the vaccine.

In another embodiment, the nucleic acid molecule comprises from about 10 ng to about 1 mg of the plasmid DNA vector or the viral vector DNA. In a particular embodiment, the nucleic acid molecule comprises from about 100 ng to about 500 µg of the plasmid or viral vector. In a more particular embodiment, the nucleic acid molecule comprises from 1 µg and 250 µg of the plasmid or viral vector. The microneedles dissolve in the animal's skin, thereby releasing the nucleic acid molecule. In an embodiment, dissolution may occur in less than about 15 minutes. In a particular embodiment, the dissolution occurs in less than about 10 minutes, or less than about 5 minutes.

In one embodiment, the dissolution occurs in less than about 1 minute. In these cases, dissolution refers to the time needed for the microneedles to be sufficiently dissolved so as to allow for patch removal (even if the patch is not actually removed at that time), although continued microneedle dissolution may occur after that.

In one embodiment, the vaccinated animals produce more than twice as many serum-neutralizing antibodies as animals vaccinated with an identical amount the nucleotides encoding the rabies G protein, but delivered as a single injection, instead of as a microneedle vaccine composition.

Optionally other compounds may be added as co-adjuvants to the microneedle formulation, including, but not limited to, alum; CpG oligonucleotides (ODN), in particular ODN 2006, 2007, 2059, or 2135 (Pontarollo R. A. et al., Vet. Immunol. Immunopath, 2002, 84: 43-59; Wernette C. M. et al., Vet. Immunol. Immunopath, 2002, 84: 223-236; Mutwiri G. et al., Vet. Immunol. Immunopath, 2003, 91: 89-103); polyA-polyU ("Vaccine Design The Subunit and Adjuvant Approach", edited by Michael F. Powell and Mark J. Newman, Pharmaceutical Biotechnology, 6: 03); dimethyldioctadecylammonium bromide (DDA) ("Vaccine Design: The Subunit and Adjuvant Approach", edited by Michael F. Powell and Mark J. Newman, Pharmaceutical Biotechnology, volume 6: 157), N,N-dioctadecyl-N',N'-bis(2-hydroxyethyl) propanediamine (such as AVRIDINE®) (Ibid, p. 148), or carbomer.

The immunogen or antigen suitable for use in the present invention may be selected from the group consisting of inactivated pathogens, attenuated pathogens, immunogenic sub-units (e.g. proteins, polypeptides, peptides, epitopes, haptens), or recombinant expression vectors, including plasmids having immunogenic inserts. In one embodiment of the present invention, the immunogen is an inactivated or killed microorganism.

In one embodiment, the immunogen is a rabies antigen, for example the vaccinia-vectored rabies antigens of RABO-RAL VRG® (Merial Limited).

In other embodiments, the antigen may be that disclosed in any, several, or all of the following documents, each of which is herein incorporated by reference in its entirety: US 2012/0269846; US 2005/0282210; U.S. Pat. No. 5,747,063; U.S. Pat. No. 8,394,384; U.S. Pat. No. 8,420,389; U.S. Pat. No. 8,603,808; U.S. Pat. No. 8,535,682; U.S. Pat. No. 8,486,418; U.S. Pat. No. 8,895,027; U.S. Pat. No. 8,871,225; U.S. Pat. No. 8,871,220; U.S. Pat. No. 8,916,371; U.S. Pat. No. 9,040,053; U.S. Pat. No. 9,101,598; and U.S. Pat. No. 9,114,108; each to Merial.

To ensure that vaccinated dogs can be easily identified during large-scale vaccination campaigns, an innocuous dye may be added to the microneedles to mark the injection site for up to one year. This method of identifying vaccinated dogs addresses a critical deficit in the monitoring of vaccination status in rabies prevention programs using conventional technologies.

Safe and Efficacious.

The dermis and the epidermis are replete with antigen-presenting cells capable of stimulating both innate and adaptive immune responses, making the skin an excellent target for administration of vaccine antigens. Moreover, the use of microneedle patches results in the generation of no sharps waste.

Overcome Maternally-Derived Antibodies.

Since DNA vaccination has been used to effectively immunize neonatal mice in the face of maternally-derived antibodies, this new method for vaccine delivery is expected to allow active immunization of entire litters of puppies, thereby decreasing the exposure of children to puppies infected with rabies.

Thermostable.

Studies performed in our laboratory have shown that influenza DNA in vaccines incorporated into microneedle patches remains stable during manufacturing and storage. Based on DNA's remarkable thermostability, we expect that rabies DNA vaccines will behave similarly.

Dose-Sparing.

Intradermal delivery of rabies vaccines is well established to be dose-sparing, as only ⅕th of the dose of the vaccine conventionally administered intramuscularly is given intradermally to human patients. Microneedle vaccination may be dose-sparing when compared to IM administration. The reduction in antigen requirements associated with use of the microneedle approach will significantly reduce the cost per dose, and thereby make it financially possible to undertake the large-scale dog vaccination programs needed to control rabies.

Simple Application.

The use of disposable microneedle device drastically reduces the potential for sharps injuries and biomedical waste. We envision that the vaccinators will apply the microneedle rabies vaccine patch to the pinna of the dog's ear or to the inner thigh area or the footpad. When the vaccine-filled microneedles are embedded into the skin, the sharps-free backing will fall off. Because the backing is composed of safe, biodegradable materials, this will pose minimal safety risk to humans, animals or the environment and risk of inappropriate re-use of needles is eliminated.

Cost-Effective.

This approach has the potential to achieve increased vaccination coverage at markedly reduced costs. Cost savings come from (i) the lower manufacturing costs of DNA vaccines compared to conventional vaccines, (ii) reduced vaccine cost due to dose-sparing of skin vaccinations, (iii) the lack of need for cold-chain storage of vaccine due to the thermostability of rabies DNA, (iv) the lack of waste disposable requirements, (v) minimal training requirements for personnel, and (vi) the expectation that the costs of mass producing microneedle patches will be the same as those for a hypodermic needle, syringe and vial.

The Microneedles

The microneedle vaccine compositions of the invention are, in one embodiment, biodegradable or bio-erodible and/or water soluble. Representative biodegradable polymers include polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly(lactide-co-caprolactone). Representative non-biodegradable polymers include polycarbonate, polyester, and polyacrylamides. Water soluble materials include sugars such as sucrose and trehalose and polymers such as polyvinylpyrrolidone, carboxymethylcellulose and polyvinyl alcohol.

The microneedles should have the mechanical strength to remain intact while being inserted into the biological barrier, while remaining in place for up to a number of days, and while being removed if they are intended to be removed (i.e., without dissolving). In embodiments where the microneedles are formed of biodegradable polymers, the microneedle must to remain intact at least long enough for the microneedle to serve its intended purpose (e.g., its conduit function for delivery of drug). The microneedles should be, in one embodiment, sterilizable using standard methods such as ethylene oxide or gamma irradiation, but may alternatively be manufactured using aseptic or controlled-bioburden processes.

The microneedles can have straight or tapered shafts. In one embodiment, the diameter of the microneedle is greatest at the base end of the microneedle and tapers to a point at the end distal the base. The microneedle can also be fabricated to have a shaft that includes both a straight (untapered) portion and a tapered portion. The needles may also not have a tapered end at all, i.e. they may simply be cylinders with blunt or flat tips. A hollow microneedle that has a substantially uniform diameter, but which does not taper to a point, is referred to herein as a "microtube." As used herein, the term "microneedle" includes both microtubes and tapered needles unless otherwise indicated.

The microneedles can be oriented perpendicular or at an angle to the substrate. In one embodiment the microneedles are oriented perpendicular to the substrate so that a larger density of microneedles per unit area of substrate can be provided. An array of microneedles can include a mixture of microneedle orientations, heights, or other parameters.

The microneedles can be formed with shafts that have a circular cross-section in the perpendicular, or the cross-section can be non-circular. For example, the cross-section of the microneedle can be polygonal (e.g. star-shaped, square, triangular), oblong, or another shape. The shaft can have one or more bores. The cross-sectional dimensions typically are between about 1 μm and 500 μm, and preferably between 50 and 300 μm in the microneedle shaft and tapering to a sharp tip with dimensions between about 0.1 μm and 20 μm, and preferably between 1 μm and 10 μm. For a microneedle with a bore, the outer diameter is typically between about 50 μm and about 300 μm in the microneedle shaft, and the inner diameter is typically between about 10 μm and about 200 μm and preferably between 30 μm and 150 μm.

In one embodiment the cross-sectional dimensions are designed to leave a residual hole (following microneedle insertion and withdrawal) of less than about 100 μm, to minimize the size of the penetration wound. The actual microneedle diameter will typically be in the range of 10 μm to 100 μm, since the holes typically contract following withdrawal of the microneedle. Larger diameter and longer microneedles are acceptable, so long as the microneedle can penetrate the biological barrier to the desired depth.

The length of the microneedles typically is between about 10 μm and 1 mm, alternatively between 100 μm and 900 μm, or alternatively between 500 μm and 800 μm. The length is selected for the particular application, accounting for both an inserted and uninserted portion. An array of microneedles can include a mixture of microneedles having, for example, various lengths, outer diameters, inner diameters, cross-sectional shapes, and spacings between the microneedles. In some applications, the "insertion depth" of the microneedles is less than about 100-150 μm, so that insertion of the microneedles into the skin does not substantially penetrate into the dermis, thereby avoiding contacting nerves which may cause pain and/or targeting vaccine delivery to the antigen-presenting cells of the epidermis. In such applications, the actual length of the microneedles typically is longer, since the portion of the microneedles distal the tip may not be inserted into the skin; the uninserted length depends on the particular device design and configuration. The actual (overall) height or length of microneedles should be equal to the insertion depth plus the uninserted length. In other applications the microneedle insertion depth is greater than 150 μm but less than 1 mm, such that vaccine delivery is to the dermis instead or in addition.

Substrate.

The substrate of the device can be constructed from a variety of materials, including metals, ceramics, semiconductors, organics, polymers, and composites. The substrate includes the base to which the microneedles are attached or integrally formed. The substrate can be adapted to fit a Luer-Lock syringe or other conventionally used drug delivery device that currently uses hypodermic needles as the barrier penetration method. The substrate can also be an adhesive backing that serves to affix the microneedle patch to the biological barrier.

In one embodiment of the device, the substrate, as well as other components, are formed from flexible materials to allow the device to fit the contours of the biological barrier, such as the skin, vessel walls, or the eye, to which the device is applied. A flexible device may facilitate more consistent penetration of some biological barriers, because penetration can be limited by deviations in the attachment surface. For example, the surface of human skin is not flat due to dermatoglyphics (i.e. tiny wrinkles) and hair. However, for some biological barriers, a rigid substrate may be preferred.

Methods for Manufacture of the Devices.

The microneedle and substrate are made by methods known to those skilled in the art. Examples include microfabrication processes, by creating small mechanical structures in silicon, metal, polymer, and other materials. These mechanical structures may be the microneedles themselves or they may be used as master structures, from which molds can be generated (for example, made of poly(dimethyl siloxane)) and microneedles fabricated using the molds to replicate the master structures. Three-dimensional arrays of hollow microneedles can be fabricated, for example, using combinations of dry etching processes; micromold creation in lithographically-defined polymers and selective sidewall electroplating; or direct micromolding techniques using epoxy mold transfers. These methods are described, for example, in U.S. Ser. No. 09/095,221, filed Jun. 10, 1998; U.S. Ser. No. 09/316,229, filed May 21, 1999; Henry, et al., "Micromachined Needles for the Transdermal Delivery of Drugs," Micro Electro Mechanical Systems, Heidelberg, Germany, pp. 494-98 (Jan. 26-29, 1998). Other methods are described in Y C Kim, J H Park, M R Prausnitz (2012) Microneedles for drug and vaccine delivery, Advanced Drug Delivery Reviews, 64:1547-1568.

The invention will now be further described by way of the following non-limiting examples.

Example 1

Figure 2:
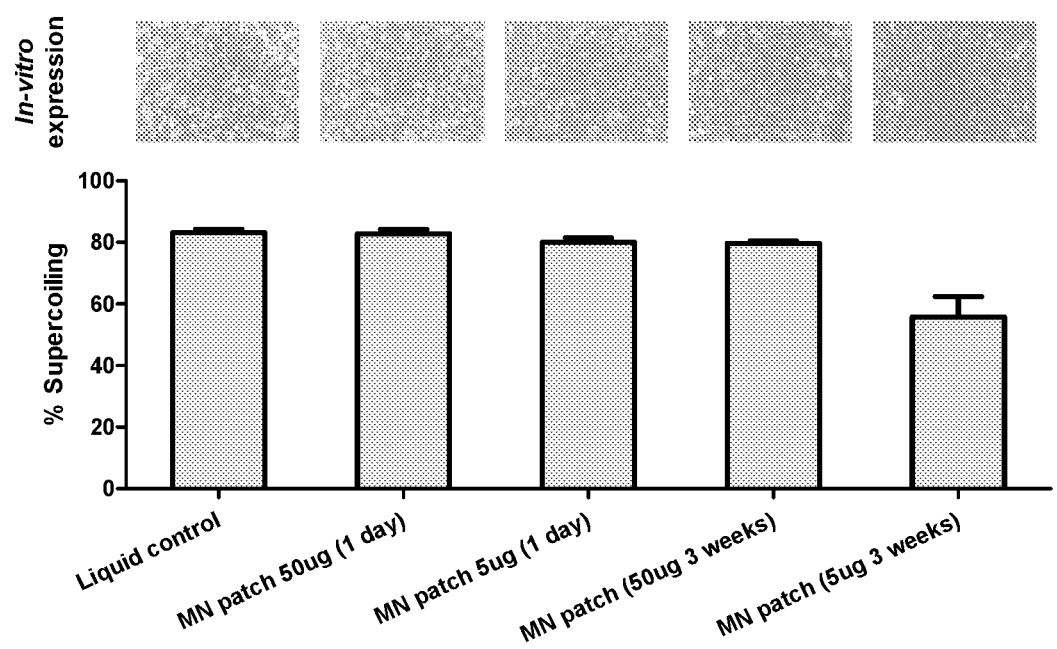
FIG. 2 shoes the percent supercoiling, as measured using agarose gel electrophoresis/staining; and the in-vitro transfection results (above each bar on the graph)
Figure 3:
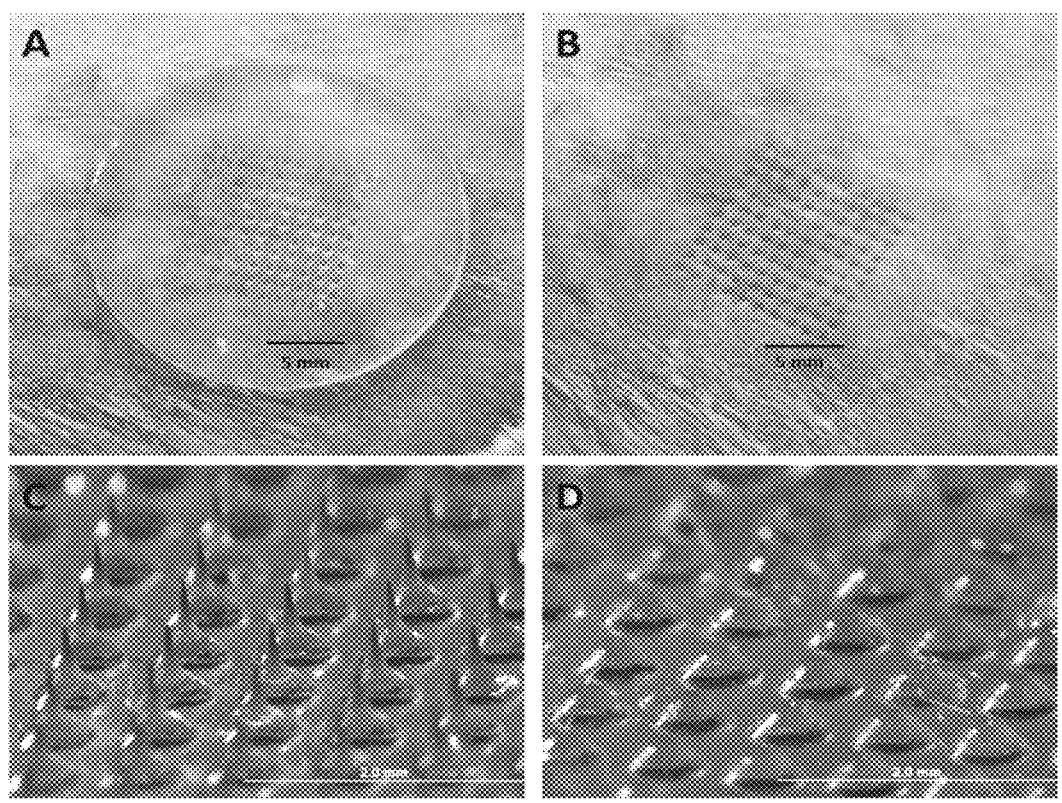
FIG. 3 the images show: (A) microneedle patch containing dye applied to a dog's ear; (B) dye delivered to the skin after patch wear time of 15 minutes; (C) the microneedle patch prior to insertion; and (D) the microneedle patch after insertion. The microneedle patches were mechanically strong (for insertion into dogs' ears), dissolved within 15 minutes, and were well tolerated.
Figure 4A:
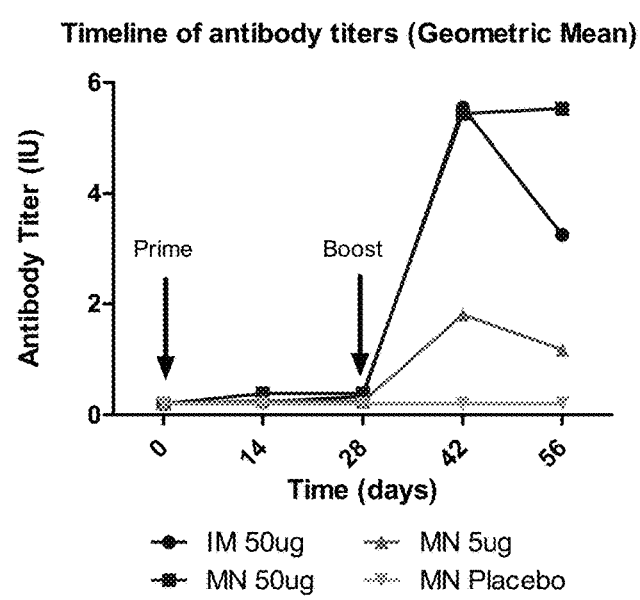
FIG. 4A is a graph showing the level of neutralizing antibodies in serum after the first and second vaccinations. Titers were measured by Rapid Fluorescent Focus Inhibition test (RFFIT); ≤0.2 are considered seronegative; ≥0.3 seropositive.
Figure 4B:
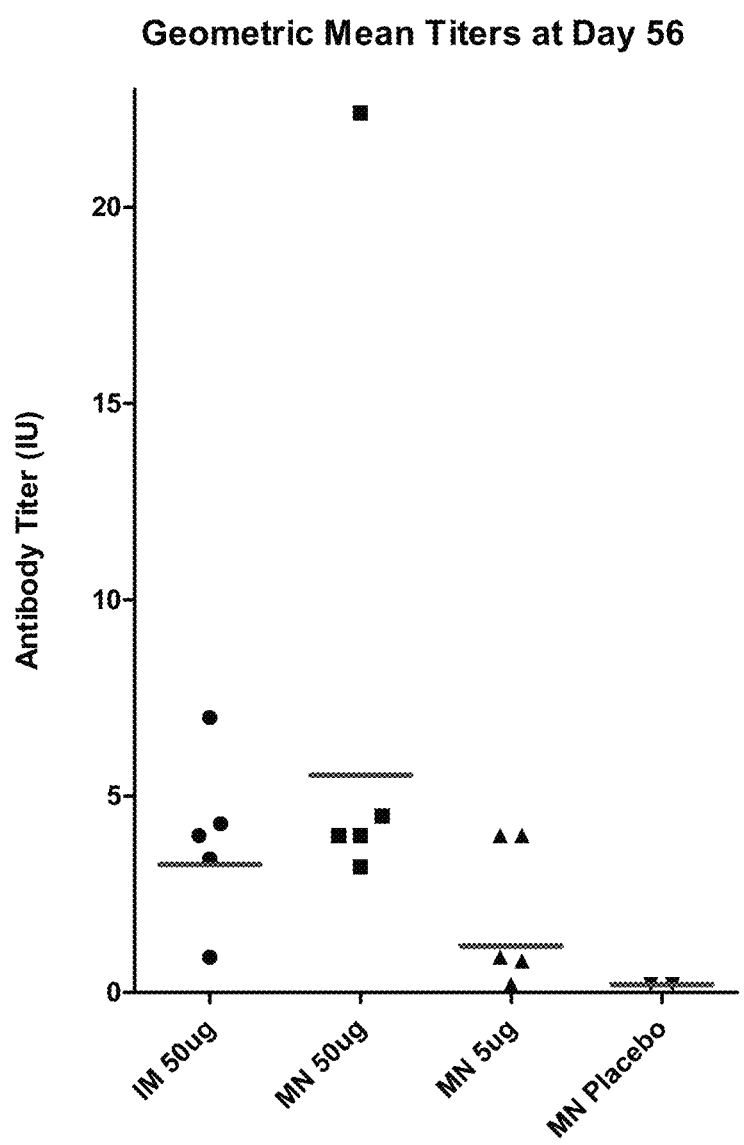
FIG. 4B is a graph showing the geometric mean titers at day 56.

Efficacy of Rabies Microneedle Vaccine Formulations in Dog

A rabies DNA microneedle vaccine was formulated, and its safety, dose sparing aspect and efficacy was evaluated in dogs. Dissolving microneedle patches are a simple, sharps-free device that could enable mass vaccination of dogs and provide vaccination methods preferred by animals and/or their owners.

Methods.

Dissolving microneedle patches were fabricated using a micromolding process, which encapsulated vaccine in a polymer and sugar matrix (using substantially the same manufacturing methods disclosed in U.S. Pat. No. 7,918,814, U.S. Pat. No. 8,257,324, U.S. Pat. No. 8,636,713 and US20080213461, each to Prausnitz). The assays used to measure DNA vaccine activity were (i) the degree of supercoiling measured using agarose gel electrophoresis; and (ii) the in-vitro expression measured by transfecting cells and staining with a rabies G antibody. Different excipients were screened to identify formulations that could maintain DNA activity upon drying as part of the micromolding process. Microneedle patches were fabricated with these excipients and stored for up to 3 weeks at 4° C. Dissolving microneedle patches were inserted into dog ears and the skin was stained with gentian violet to measure efficiency of insertion.

Results.

Suitable formulations remained stable at 3 weeks at 4° C. storage, as shown by little or no loss of supercoiling and successful in vitro transfection (FIGS. 2 and 3). The microneedles were mechanically strong and inserted well into dog ears as seen by counting the number of holes created in the skin upon staining (FIG. 3). The needles dissolved completely within 15 minutes of insertion.

Conclusions.

Rabies DNA vaccine has been successfully formulated into a dissolving microneedle patch that can be stored for at least 3 weeks at 4° C. without significant loss in activity. Upon insertion into dog ears, the needles dissolve within 15 minutes, thus enabling simple, sharps-free administration.

Detailed Materials and Methods.

Seventeen 5 to 11 month old beagles were vaccinated twice, 28 days apart, with 50 µg DNA rabies vaccine via conventional needle (n=5), 50 µg DNA rabies vaccine via microneedle array (n=5), 5 µg DNA rabies vaccine via microneedle array (n=5) or an untreated microneedle array (n=2). Dogs vaccinated via conventional needle were injected intramuscularly in the rear leg. Dogs vaccinated via microneedle array were vaccinated in the ear pinna. All vaccinations were given on the right side for the first vaccination (V1) and on the left side for the second vaccination (V2). The dogs were randomized to group by gender and age, and the groups were commingled throughout the study. The dogs were observed for local injection site reactivity on the day of vaccination, daily for the first three days following each vaccination and intermittently in the subsequent days for any dogs with reactions persisting more than 3 days. Injection sites were monitored for erythema, wheal formation, swelling, pain and ulceration. Rectal temperatures were taken on the day of vaccination and on the first three days after each vaccination. Blood was collected on days −3, 14, 25, 42 and 56, and serum samples were submitted to Atlanta Health Associates for analysis of rabies antibody titers using the rapid fluorescent focus inhibition test (RFFIT).

Detailed Results.

The dogs in each vaccination group were evaluated for tolerance of injection and injection site reactions. Dogs were considered intolerant of injection if they vocalized, withdrew or tried to bite upon injection. At V1 dogs in the conventional needle group were least tolerant to injection while at V2 one dog in the microneedle array 5 µg group was intolerant to injection (Table 1). Dogs in the untreated microneedle array and microneedle array 50 µg groups were most tolerant of injection with all animals in these groups being tolerant for both vaccinations. None of the responses to injection were greater than what would normally be anticipated following vaccination.

None of the dogs in the conventional needle group experienced injection site reactions, while all of the dogs in the microneedle array 5 µg and in the microneedle array 50 µg groups experienced injection site reactions (Table 2).

TABLE 1

Tolerance of injection

| Vaccination Group | # dogs tolerant of injection | |
|---|---|---|
| | V1 (Day 0) | V2 (Day 28) |
| Conventional Needle 50 µg (n = 5) | 2 | 5 |
| Microneedle Array 5 µg (n = 5) | 5 | 4 |
| Microneedle Array 50 µg (n = 5) | 5 | 5 |
| Untreated Microneedle Array (n = 2) | 2 | 2 |

TABLE 2

Injection site reactions by group

| Vaccination Group | # dogs with injection site reactions | | |
|---|---|---|---|
| | Overall | After V1 | After V2 |
| Conventional Needle 50 µg (n = 5) | 0 | 0 | 0 |
| Microneedle Array 5 µg (n = 5) | 5 | 4 | 5 |
| Microneedle Array 50 µg (n = 5) | 5 | 5 | 5 |
| Untreated Microneedle Array (n = 2) | 1 | 1 | 0 |

Injection sites were observed for erythema (redness), wheal formation, swelling, pain and ulceration. The types of reactions (Table 3) and the duration of injection site reactions (Tables 4-7) were compared among groups. All reactions were resolved within 7 days. The most common injection site reaction was erythema, occurring most frequently in the microneedle array 5 µg and microneedle array 50 µg groups (Table 3). Most erythema resolved within 3 or 4 days after V1, with resolution occurring in 7 days for one dog (Table 4). After V2, the erythema in 5 of the 10 dogs resolved within 4 days while the erythema in the other 5 dogs resolved within 7 days (Table 5). Wheal formation occurred in all of the microneedle array groups and resolved within 2 days (Tables 6 & 7). No swelling, pain on palpation or ulceration was observed in any group, and all dogs had rectal temperatures within normal limits throughout the study.

TABLE 3

Types of injection site reactions

| Vaccination Group | Number of dogs with injection site reactions | | | | |
|---|---|---|---|---|---|
| | Erythema | Wheal formation | Swelling | Pain upon palpation | Ulceration |
| Conventional Needle 50 µg (n = 5) | 0 | 0 | 0 | 0 | 0 |
| Microneedle Array 5 µg (n = 5) | 5 | 2 | 0 | 0 | 0 |
| Microneedle Array 50 µg (n = 5) | 5 | 1 | 0 | 0 | 0 |
| Untreated Microneedle Array (n = 2) | 1 | 1 | 0 | 0 | 0 |

TABLE 4

Duration of erythema after first vaccination

| Vaccination Group | Number of Dogs with Erythema | Number Resolving in: | | |
|---|---|---|---|---|
| | | 3 Days | 4 Days | 7 Days |
| Conventional Needle 50 µg (n = 5) | 0 | — | — | — |
| Microneedle Array 5 µg (n = 5) | 4 | 2 | 1 | 1 |
| Microneedle Array 50 µg (n = 5) | 5 | 2 | 3 | — |
| Untreated Microneedle Array (n = 2) | 1 | 1 | — | — |

TABLE 5

Duration of erythema after second vaccination

| Vaccination Group | Number of Dogs with Erythema | Number Resolving in: | | | |
|---|---|---|---|---|---|
| | | 2 Days | 3 Days | 4 Days | 7 Days |
| Conventional Needle 50 µg (n = 5) | 0 | — | — | — | — |
| Microneedle Array 5 µg (n = 5) | 5 | — | 1 | — | 4 |
| Microneedle Array 50 µg (n = 5) | 5 | 1 | 1 | 2 | 1 |
| Untreated Microneedle Array (n = 2) | 0 | — | — | — | — |

TABLE 6

Duration of wheal reaction after first vaccination

| Vaccination Group | Number of Dogs with Wheal | Number Resolving in: 2 Days |
|---|---|---|
| Conventional Needle 50 µg (n = 5) | 0 | — |
| Microneedle Array 5 µg (n = 5) | 1 | 1 |
| Microneedle Array 50 µg (n = 5) | 1 | 1 |
| Untreated Microneedle Array (n = 2) | 1 | 1 |

TABLE 7

Duration of wheal after second vaccination

| Vaccination Group | Number of Dogs with Wheal | Number Resolving in: 2 Days |
|---|---|---|
| Conventional Needle 50 µg (n = 5) | 0 | — |
| Microneedle Array 5 µg (n = 5) | 1 | 1 |
| Microneedle Array 50 µg (n = 5) | 0 | — |
| Untreated Microneedle Array (n = 2) | 0 | — |

Serological Response to Vaccination.

The serum of the dogs was analyzed for antibodies to rabies using the rapid fluorescent focus inhibition test (RFFIT). A titer of 0.2 IU/ml or lower was considered seronegative. All animals were seronegative for antibodies to rabies prior to vaccination. Dogs in the untreated microneedle array group remained seronegative throughout the study (Table 8). For the conventional needle 50 µg and microneedle array 50 µg groups, all dogs were seropositive by day 42 of the study (Table 8). For the microneedle array 5 µg group, one dog remained seronegative throughout the study. The day of highest geometric mean titer was day 42 for all groups except microneedle array 50 µg group, which had its highest mean titer on day 56 (Table 9). Of the groups receiving rabies vaccine, the microneedle array 5 µg had the lowest geometric mean titers on all but day 14 when the conventional needle group had a lower geometric mean titer.

TABLE 8

Dogs seropositive (0.3 IU/ml or greater) for rabies antibody

| Vaccination Group | Day of Study | | | | |
|---|---|---|---|---|---|
| | Pre-screen | 14 | 25 | 42 | 56 |
| Conventional Needle 50 µg (n = 5) | 0 | 1 | 3 | 5 | 5 |
| Microneedle Array 5 µg (n = 5) | 0 | 2 | 1 | 4 | 4 |
| Microneedle Array 50 µg (n = 5) | 0 | 2 | 2 | 5 | 5 |
| Untreated Microneedle Array (n = 2) | 0 | 0 | 0 | 0 | 0 |

TABLE 9

Geometric mean rabies antibody titer (IU/ml)

| Vaccination Group | Day of Study | | | | |
|---|---|---|---|---|---|
| | Pre-screen | 14 | 25 | 42 | 56 |
| Conventional Needle 50 µg (n = 5) | 0.2 | 0.24 | 0.33 | 5.55 | 3.26 |
| Microneedle Array 5 µg (n = 5) | 0.2 | 0.26 | 0.24 | 1.81 | 1.18 |
| Microneedle Array 50 µg (n = 5) | 0.2 | 0.39 | 0.39 | 5.44 | 5.53 |
| Untreated Microneedle Array (n = 2) | 0.2 | 0.2 | 0.2 | 0.2 | 0.2 |

Conclusions.

Compared to conventional needle administration, the microneedle array met the criteria for serological response when administered at a dose of 50 µg. Dogs in the conventional needle group were less tolerant of injection than dogs in all other groups during V1. The three dogs that were not tolerant of injection were six months younger than the other two dogs in the group, which may account for the difference in response.

The serology results revealed that comparable mean titers were achieved for the microneedle array 50 µg and conventional needle 50 µg groups. When comparing the mean titers of the microneedle array 5 µg and 50 µg groups, there appeared to be a dose effect where vaccination with the microneedle array at a dose of 50 µg yielded higher mean titers than vaccination with the microneedle array at a dose of 5 µg.

Accordingly, a plasmid DNA rabies vaccine has been successfully formulated into a microneedle patch that was well tolerated and at least as immunogenic as conventional needle and syringe injection. Importantly, four out of the five animals were seropositive at day 56. The patches were left on the skin for 15 minutes, but additional formulations will allow quicker dissolution times, including less than about one minute.

REFERENCES

WHO. Rabies vaccines: WHO position paper. Weekly epidemiological record. No. 32, 2010; 85. p. 209-320.

Hethcote, H W. An immunization model for a heterogeneous population. Theoretical Population Biology 1978; 14:338-349.

Having thus described in detail embodiments of the present invention, it is to be understood that the invention defined by the above paragraphs is not to be limited to particular details set forth in the above description as many apparent variations thereof are possible without departing from the spirit or scope of the present invention.

What is claimed is:

1. A safe and effective microneedle Rabies virus vaccine composition, which when administered to the pinna of an animal's ear elicits in said animal a safe and protective immune response against subsequent virulent Rabies virus challenge, comprising an immunogen comprising:
    (a) an effective amount of a plasmid DNA vector expressing in vivo in said animal a protective Rabies G antigen,
    (b) an effective amount of an attenuated recombinant viral vector expressing in vivo in said animal a protective Rabies G antigen, or
    (c) an effective amount of a protective Rabies G polypeptide; and
    a sugar and a bioerodible polymer; and
    wherein the composition is formulated as bio-absorbable microneedles; and
    wherein the composition is stable for at least 3 weeks at 4° C.

2. The vaccine composition of claim 1, wherein the attenuated vector is an orthopox or an avipox virus.

3. The vaccine composition of claim 2, wherein the orthopox or avipox vector is a vaccinia, a canarypox, or a fowlpox virus.

4. The vaccine composition of claim 3, wherein the vector expresses in vivo in the animal a Rabies G protein having the amino acid sequence as set forth in SEQ ID NO: 1.

5. The vaccine composition of claim 1, wherein the immunogen consists of a plasmid DNA vector, which contains and expresses in vivo in said animal a Rabies G protein having the sequence as set forth in SEQ ID NO: 1.

6. The vaccine composition of claim 5, wherein the plasmid is present in an effective amount between at least 5 μg and about 50 μg.

7. The vaccine composition of claim 6, wherein the microneedles dissolve in the animal's skin, thereby releasing the plasmid DNA, in less than about 15 minutes.

8. The vaccine composition of claim 1, wherein the vaccinated animal produces more than twice as many serum-neutralizing antibodies as animals vaccinated with an identical amount the composition, but delivered as a single injection, instead of as a microneedle vaccine composition.

9. A method for vaccinating an animal against Rabies comprising the step of administering an effective amount of the vaccine composition of claim 1 by pressing the microneedles into the skin of the ear pinna of said animal and allowing the microneedles to dissolve for less than about 15 or about 10 or about 5 minutes, thereby vaccinating said animal.

10. The method of claim 9, wherein the animal is a canine or a feline animal and the microneedles dissolve in less than about 15 minutes.

11. The method of claim 10, wherein the immunogen is a vector selected from a vaccinia, a canarypox, or a fowlpox virus.

12. The method of claim 11, wherein the vector expresses in vivo in the animal a Rabies G protein having the amino acid sequence as set forth in SEQ ID NO: 1.

13. The method of claim 11, wherein a single dose of the vaccine composition is adequate to protect from subsequent challenge greater than 80% of the animals receiving a single dose, and greater than 95% of the animals receiving a second, booster dose.

14. The method of claim 9, which is a dose-sparing method, which allows the use of less than one-half of the amount of immunogen required to elicit a protective immune response using a conventional single needle administration.

15. The method of claim 14, wherein the immunogen is a modified live vaccinia virus and wherein the Rabies G antigen has the sequence as set forth in SEQ ID NO: 1.

16. The method of claim 14, wherein the immunogen is a plasmid DNA and wherein the Rabies G antigen has the sequence as set forth in SEQ ID NO: 1.

17. The method of claim 9, comprising a first dose and a second dose.

18. The method of claim 17, wherein the first and second doses have the same compositions, wherein the second dose is administered to the animal about 28 days after the first dose; and wherein the average Rabies antibody titer is greater than or equal to 5 IU at day 42 after the first dose.

19. The method of claim 18, wherein the animal is a canine animal; and wherein the average Rabies antibody titer is greater than or equal to about 4 IU at day 56 after the first dose.

20. The method of claim 14, wherein the immunogen comprises an effective amount of a Rabies G polypeptide having the sequence as set forth in SEQ ID NO: 1.

21. The vaccine composition of claim 3, wherein the microneedles dissolve in the animal's skin, thereby releasing the attenuated vector, in less than about 15 minutes.

22. The vaccine composition of claim 1, wherein the immunogen is a protective Rabies G polypeptide, and wherein the microneedles dissolve in the animal's skin, thereby releasing the polypeptide, in less than about 15 minutes.

23. The method of claim 10, wherein the immunogen is an effective amount of a DNA plasmid containing and expressing in vivo in said animal an effective amount of a Rabies G polypeptide.

24. The method of claim 10, wherein the immunogen is an effective amount of a Rabies G polypeptide.

25. The vaccine composition of claim 1, wherein the immunogen consists essentially of the plasmid DNA vector expressing in vivo in said animal a protective Rabies G antigen.

26. The vaccine composition of claim 1, wherein the immunogen consists essentially of the effective amount of the attenuated recombinant viral vector expressing in vivo in said animal a protective Rabies G antigen.

27. The vaccine composition of claim 1, wherein the immunogen consists essentially of the effective amount of the protective Rabies G polypeptide.

28. The vaccine composition of claim 25, wherein the immunogen consists of the plasmid DNA vector present in an amount of 5 µg to less than 50 µg.

* * * * *